(12) United States Patent
Lundstedt et al.

(10) Patent No.: US 7,186,748 B2
(45) Date of Patent: Mar. 6, 2007

(54) N-PHENYLPYRROLE GUANIDINE DERIVATIVES AS MELANOCORTIN RECEPTOR LIGANDS

(75) Inventors: Torbjörn Lundstedt, Uppsala (SE); Anna Skottner, Ekerö (SE); Arne Boman, Uppsala (SE); Per Andersson, Sollentuna (SE); Elisabeth Seifert, Uppsala (SE); Victor Andrianov, Riga (LV)

(73) Assignee: Action Pharma A/S, Arhus N (DK)

( * ) Notice: Subject to any disclaimer, the term of this patent is extended or adjusted under 35 U.S.C. 154(b) by 114 days.

(21) Appl. No.: 10/484,444

(22) PCT Filed: Aug. 6, 2002

(86) PCT No.: PCT/GB02/03620

§ 371 (c)(1),
(2), (4) Date: Jan. 29, 2004

(87) PCT Pub. No.: WO03/013509

PCT Pub. Date: Feb. 20, 2003

(65) Prior Publication Data

US 2004/0254093 A1    Dec. 16, 2004

(30) Foreign Application Priority Data

Aug. 6, 2001  (GB)  .................. 0119172.5

(51) Int. Cl.
*A61K 31/402*  (2006.01)
*C07D 207/335*  (2006.01)

(52) U.S. Cl. .................. 514/427; 548/561; 534/738
(58) Field of Classification Search ................ 548/561; 514/427; 534/738
See application file for complete search history.

(56) References Cited

U.S. PATENT DOCUMENTS 6,599,943 B1 *  7/2003  Wikberg et al. ............ 514/634
2003/0232843 A1 * 12/2003  Cole et al. .................. 514/256

(Continued)

FOREIGN PATENT DOCUMENTS

WO    98 23267 A    6/1998

(Continued)

OTHER PUBLICATIONS

Garuti, L., et al., "Amidinoidrazoni di formilesteri e formiltioesteri con substrati N-eterociclici aromatici," Farmaco, Edizione Scientifica, vol. 36(9), pp. 779-784 (Sep. 1981); English Summary at p. 779, lines 4-5; p. 780 (compound (I)).*

(Continued)

*Primary Examiner*—Kamal A. Saeed
*Assistant Examiner*—Jason M. Nolan
(74) *Attorney, Agent, or Firm*—Bacon & Thomas

(57) ABSTRACT

The present invention provides novel compounds of the general Formula (I) as ligands to the melanocortin receptors and/or for treatment of disorders in the melanocortin system:

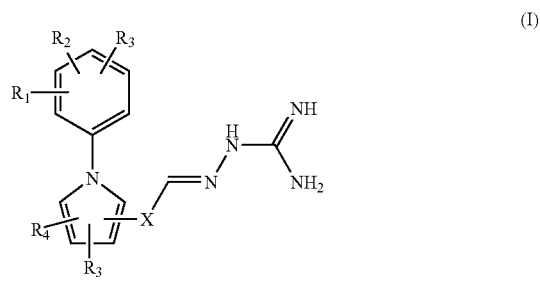

(I)

wherein X is $(CH_2)_n$ where n is 0, 1 or 2;
$R_1$, $R_2$, $R_3$, $R_4$ and $R_5$ may be the same or different and are selected from hydrogen, halogen, alkyl having 1 to 5 carbon atoms, alkoxy having 1 to 5 carbon atoms, hydroxy, alkylsulphonyloxy, cyano, nitro, trihaloalkyl, sulpho or one of the structures given in Scheme 1; or two of $R_1$, $R_2$, $R_3$, $R_4$ and $R_5$ may together form a methylenedioxy or ethylenedioxy moiety;

Scheme 1

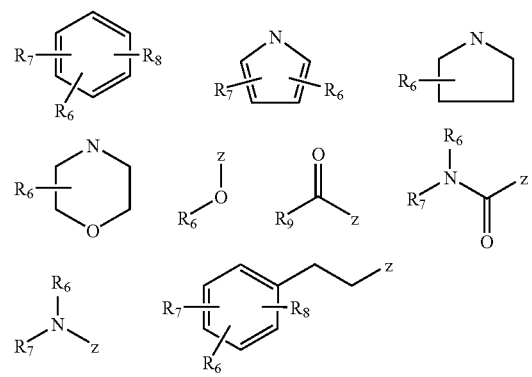

$R_6$, $R_7$, $R_8$ and $R_9$ are the same or different and are selected from hydrogen, halogen, alkyl having 1 to 5 carbon atoms, alkoxy having 1 to 5 carbon atoms, hydroxy, amines (primary, secondary or tertiary) having 0, 1 or 2 carbon atoms, cyano, nitro, trihaloalkyl, amide or sulpho, and z where shown represents the point of attachment of the residue to the phenyl or pyrrole ring;
and the pharmacologically active salts thereof.

19 Claims, No Drawings

U.S. PATENT DOCUMENTS

2004/0019094 A1* 1/2004 Lundstedt et al. .......... 514/406
2004/0106682 A1* 6/2004 Lundstedt et al. .......... 514/635

FOREIGN PATENT DOCUMENTS

| WO | 01 25192 A | 4/2001 |
| WO | 01/55109 A1 | 8/2001 |
| WO | 02 11715 A | 2/2002 |
| WO | 02 12178 A | 2/2002 |

OTHER PUBLICATIONS

Caplus Abstract Accession No. 1981:614890 & Farmaco, Ed. Sci. vol. 36, No. 9, 1981, L. Garuti et al., "Substances with antiviral activity. . . ", pp. 779-784 (see abstract).

Caplus Abstract Accession No. 1981:515189 & Farmaco, Ed Sci. vol. 36, No. 6, 1981, L. Garuti et al., "Study on substances of antiviral activity. . . ", pp. 393-399 (see abstract).

Caplus Abstract Accession No. 1975:514138 & Farmaco, Ed. Sci vol. 30, No. 6, 1975, A. Andreani et al., "Substances with antiviral activity. . .", pp. 440-448 (see abstract).

* cited by examiner

N-PHENYLPYRROLE GUANIDINE DERIVATIVES AS MELANOCORTIN RECEPTOR LIGANDS

The present invention relates to phenyl pyrrole aminoguanidines. It further relates to the use of these guanidines for the treatment of obesity, anorexia, inflammation, mental disorders and other diseases associated with the melanocortin receptors or related systems, e.g. the melanocyte stimulating hormones.

A number of large linear and cyclic peptides are known in the art which show high specific binding to melanocortin (MC) receptors. The agonistic and/or antagonistic properties of these peptides are also known. See for example "Melanocortin Receptor ligands and methods of using same" by Dooley, Girten and Houghten (WO99/21571).

A number of low molecular weight compounds are known, e.g. isoquinolines, spiropyridines and benzimidazoles, which show activity on the MC-receptors. See "Isoquinoline compound melanocortin receptor ligands and methods of using same" by Basu et al, Trega Biosciences Inc. (WO 99/55679), "Spiropiperidine derivatives as melanocortin receptor agonists" by Nargung, Ye, Palucki, Bakshi, Patchett and van der Ploeg (WO 99/64002) and "Melanocortin receptor-3 ligands to treat sexual dysfunction" by Dines et al. (WO0105401). See also WO0074679, WO0058361, WO0218327, WO0212166, WO0155106, WO0155107, WO0155109, WO0211715 and WO0212178 for additional compounds acting on the melanocortin receptors.

However, there is still a large need to provide low molecular weight compounds showing agonistic or antagonistic properties to the melanocortin receptors. The compounds of the present invention are structurally different from the above-mentioned compounds and, consequently, constitute a new class of compounds that show activity to the MC-receptors.

A compound previously known in the art, which is similar to the presented compounds, is given below (see e.g. WO98/23267):

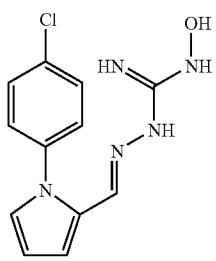

This hydroxyguanidine has proven activity against xanthine oxidase/xanthine dehydrogenase enzymes. Therefore it is very surprising that the phenyl pyrrole benzylideneamino guanidine compounds in the present invention show affinity to the melanocortin receptors as agonists and/or antagonists.

One aspect of the present invention is therefore to provide low molecular weight compounds showing activity on melanocortin receptors and which may be taken up after peroral administration and which may penetrate well through the blood brain barrier.

The present invention provides novel compounds of the general formula (I) and their tautomeric forms:

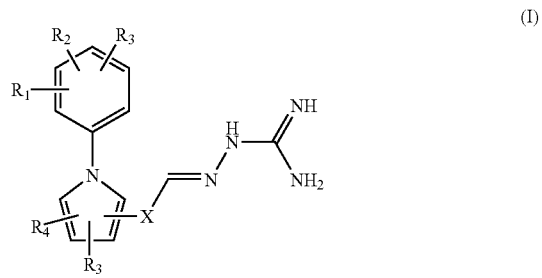

wherein X is $(CH_2)_n$ where n is 0, 1 or 2;

$R_1$, $R_2$, $R_3$, $R_4$ and $R_5$ may be the same or different and are selected from hydrogen, halogen, alkyl having 1 to 5 carbon atoms, alkoxy having 1 to 5 carbon atoms, hydroxy, alkylsulphonyloxy, cyano, nitro, trihaloalkyl, sulpho or one of the structures given in Scheme 1; and/ or two of $R_1$, $R_2$, $R_3$, $R_4$ and $R_5$ may together form a methylenedioxy or ethylenedioxy moiety (preferably such methylenedioxy or ethylenedioxy moieties are formed using $R_4$ and $R_5$ and/or two of $R_1$, $R_2$ and $R_3$);

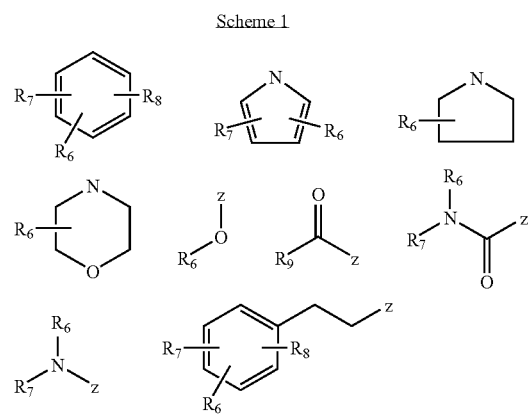

Scheme 1

$R_6$, $R_7$, $R_8$ and $R_9$ are the same or different and are selected from hydrogen, halogen, alkyl having 1 to 5 carbon atoms, alkoxy having 1 to 5 carbon atoms, hydroxy, amines (primary, secondary or tertiary) having 0, 1 or 2 carbon atoms, cyano, nitro, trihaloalkyl, amide or sulpho, and z where shown represents the point of attachment of the residue to the phenyl or pyrrole ring;

and the pharmacologically active salts thereof.

The term halogen includes fluoro, chloro, bromo and iodo.

The term "alkyl" includes straight or branched hydrocarbon chains. The term "alkoxy" includes straight and branched chain alkoxy groups.

Preferably, the "allyl having 1 to 5 carbon atoms" is a lower alkyl such as methyl, ethyl, propyl, isopropyl or tert-butyl.

Preferably, the "alkoxy having 1 to 5 carbon atoms" is a lower alkoxy such as methoxy, ethoxy, propoxy, iso-propoxy or tert-butoxy.

The term trihaloalkyl includes straight or branched hydrocarbon chains, preferably having 1 to 5 carbon atoms, and includes trichloroalkyl and trifluoroalkyl.

Preferably, the trihaloalkyl is trihalomethyl, trihaloethyl, trihalopropyl or trihaloiso-propyl.

Furthermore, it should be noted that the Scheme 1 residues may be attached to the carbon backbone of the compound of general formula (I) at any suitable point within the compound of Scheme 1, preferably at the 1, 2 or 3 position.

The compounds of formula (I) have basic properties and, consequently, they may be converted to their therapeutically active acid addition salts by treatment with appropriate physiologically acceptable acids, e.g. inorganic acids such as hydrochloric, hydrobromic, hydriodic, sulphuric, nitric and phosphoric acid, or organic acids such as acetic, propanoic, glycolic, lactic, malonic, succinic, fumaric, tartaric, citric, pamoic, oxalic and para-toluene-sulphonic acid.

Conversely, the salt form may be converted into the free base form by treatment with alkali.

The present invention relates to novel aromatic amines. Compounds of the present invention have been biologically tested in the melanocortin system and have surprisingly been shown to be capable of binding to melanocortin receptors as well as showing activity in functional assays.

Compounds of the present invention are either agonists or antagonists of a specific MC-receptor or of a number of MC-receptors, e.g. MC1, MC3, MC4 or/and MC5 receptors.

The MC-receptors belong to the class of G-protein coupled receptors which are all built from a single polypeptide forming 7 transmembrane domains. Five such receptors types, termed MC1, MC2, MC3, MC4 and MC5, have been described. The MC receptor's signaling is mainly mediated via cAMP but also other signal transduction pathways are known. They are distinctly distributed in the body.

MC-receptors are linked to a variety of physiological actions that are thought to be mediated by distinct subtypes of the MC-receptors. In many cases, however, it is not entirely clear which of the subtypes is responsible for the effect.

It has long been known that MSH-peptides may affect many different processes such as motivation, learning, memory, behaviour (including feeding and sexual), inflammation (including immunostimulatory and immunosuppressive), body temperature, pain perception, blood pressure, heart rate, vascular tone, brain blood flow, trophic effects in different organs, nerve growth, placental development, endocrine and exocrine functions, aldosterone synthesis and release, thyroxin release, spermatogenesis, ovarian weight, prolactin and FSH secretion, effects or other hormones, uterine bleeding in women, sebum and pheromone secretion, blood glucose levels, natriuresis, intrauterine foetal growth, as well as other events surrounding parturition (Eberle, AN: The melanotropins: Chemistry, physiology and mechanisms of action. Basel: Karger, Switzerland. 1988, ISBN 3-8055-4678-5; Gruber, and Callahan, Am. J. Physiol. 1989, 257, R681–R694; De Wildt et al., J. Cardiovascular Pharmacology. 1995, 25, 898–905), as well as inducing natriuresis (Lin et al., Hypertension. 1987, 10, 619–627).

It is also well-known that the immunomodulatory action of α-MSH includes both immuno-stimulatory and immuno-suppressive effects. Several studies have shown that α-MSH antagonizes the effects of pro-inflammatory cytokines such as IL-1α, IL-1β, IL-6 and TNFα, and induces the production of the anti-inflammatory cytokine, IL-10 (for review see Catania & Lipton, 1993).

Eating behaviour is regulated by a complex network of physiological regulatory pathways that involve both the central nervous system and peripheral sites. Factors such as leptin, insulin, NPY (neuropeptide Y), orexins, CRF (Corticotropin-Releasing Factor, release hormone) and melanocortic peptides (Schwartz; Nature Medicine 1998, 4, 385–386) are known to control the amount of food intake both during short and long term, which may affect body weight, body fat mass and growth rate. Recent studies have shown a role of MC-receptors, especially the MC4 receptor, for control of food intake, and there is evidence indicating that the melanocortins and the MC4 receptor are important factors downstream of leptin. Intracerebroventricular injections of the melanocortic peptides α-MSH and ACTH(1–24) have been shown to markedly inhibit feeding (Poggioli et al., Peptides, 1986, 7, 843–848; Vergoni et al., Neuropeptides, 1986, 7, 153–158).

The MC5-receptor has recently been attributed a role in control of exocrine gland function (van der Kraan, et al., Endocrinol. 1998, 139, 2348–2355; Chen et al., Cell. 1997, 91, 789–798).

In addition, the melanocortic peptides have distinct effects on sexual functions in that they cause erection in males (Donovan, Psychol. Med. 1978, 8, 305–316), presumably mediated by a central agonistic effect of the peptide on MC-receptors. It has also been shown that a MC-receptor blocker could inhibit the erectogenic effect of melanocortic peptides (Vergoni et al., Eur. J. Pharmacol, 1998, 362; 95–101).

Compounds of formula (I) and/or their pharmaceutically acceptable salts have valuable pharmacological properties, making them useful for the treatment of mental disorders such as psychoses, depression, anxiety, senile dementia, Alzheimer's disease, drug abuse disorders and eating disorders such as anorexia and bulimia.

Compounds of formula (I) and/or their pharmaceutically acceptable salts have valuable pharmacological properties, making them useful for the treatment of dysfunctions of the endocrine system and other hormonal systems such as excessive menstruations, endometriosis, events related to parturition, dysfunctions related to prolactin, dysfunctions related to growth hormone, dysfunctions related to testosterone, dysfunctions related to estrogen, dysfunctions related to glucocorticoids, dysfunctions related to luteinizing hormone and follicle stimulating hormone, inducing abortion, for prevention of abortion and/or for treatment of events related to parturition.

Compounds of formula (I) and/or their pharmaceutically acceptable salts have valuable pharmacological properties, making them useful for the treatment of sexual functions/dysfunctions such as inducing erection in man, to induce erection in animal breeding, to stimulate intercourse in animals which are difficult to mate, in particular rare species or valuable strains, pets, cats, dogs, horses or to reduce sexual behaviour in animals, e.g. for pets, cats etc., to treat impotence and disorders related to sexual drive, including lack of sexual drive or abnormal sexual drive in both men and women.

Compounds of formula (I) and/or their pharmaceutically acceptable salts have valuable pharmacological properties, making them useful for the treatment of inflammation such as inflammations related to the production of nitric oxide, inflammation related to increased amounts (upregulated amounts) of inducible nitric oxide synthase, inflammation related to activation of transcriptional activators, inflammation related to nuclear factor kappa beta, inflammation related to macrophages, neutrophils, monocytes, keratinocytes, fibroblasts, melanocytes, pigment cells and endothelial cells, inflammation related to increased production and/or release of inflammatory cytokines, such as e.g. interleukins, in particular interleukin 1 (IL-1), interleukin 6 (IL-6) and tumor necrosis factor a (TNF-α).

In the present specification, "increased production" refers to increased formation, increased release, or increased amount of an endogenous compound locally, regionally or systemically in a patient compared to the amount of said endogenous compound in a healthy individual. In the present specification, "upregulated" refers to an increased activity or amount of the compound compared with that in a healthy individual.

In the present specification, "decreased production" refers to decreased formation, decreased release, or decreased amount of an endogenous compound in a patient compared to the amount of said endogenous compound in a healthy individual. In the present specification, "downregulated" refers to a decreased activity or amount of the compound compared with that in a healthy individual.

In particular, positive treatment effects or preventive effects may be seen in conditions where inflammation or an inflammatory-like condition is caused by or being associated with one or more of the following: allergy, hypersensitivity, bacterial infection, viral infection, inflammation caused by toxic agent, fever, autoimmune disease, radiation damage by any source including UV-radiation, X-ray radiation, γ-radiation, α- or β-particles, sun burns, elevated temperature or mechanical injury. Moreover, inflammation due to hypoxia, which is optionally followed by reoxygenation of the hypoxic area, is typically followed by severe inflammation, which condition may be positively affected by treatment with a compound of the invention.

In very specific embodiments of the invention, a compound of the invention may be administered for the prevention or therapeutic treatment of inflammatory diseases of the skin (including the dermis and epidermis) of any origin, including skin diseases having an inflammatory component. Specific examples of this embodiment of the invention include treatment of contact dermatitis of the skin, sunburns of the skin, burns of any cause, and inflammation of the skin caused by chemical agents, psoriasis, vasculitis, pyoderma gangrenosum, discoid lupus erythematosus, eczema, pustulosis palmo-plantaris, and phemphigus vulgaris.

Also comprised by the invention is the administration of a compound of formula (I) or a pharmacologically acceptable salt thereof for the treatment of an inflammatory disease in the abdomen, including an abdominal disease having an inflammatory component. Specific examples of the treatment of such a disease with a compound of the invention are gastritis, including one of unknown origin, gastritis perniciosa (atrophic gastritis), ulcerous colitis (colitis ulcerosa), morbus Crohn, systemic sclerosis, ulcus duodeni, coeliac disease, oesophagitis and ulcus ventriculi.

Comprised by the invention is also the administration of a compound of formula (I) or a pharmacologically acceptable salt thereof for the treatment of systemic or general and/or local immunological diseases, including those of an autoimmune nature, and other inflammatory diseases of a general nature. Specific examples include treatment of rheumatoid arthritis, psoriatic arthritis, systemic sclerosis, polymyalgia rheumatica, Wegener's granulomatosis, sarcoidosis, eosinophilic fasceitis, reactive arthritis, Bechterew's disease, systemic lupus erythematosus, arteritis temporalis, Behcet's disease, morbus Burger, Good Pastures' syndrome, eosinophilic granuloma, fibromyalgia, myositis, and mixed connective tissue disease. Included therein is also arthritis, including arthritis of unknown origin.

Further included in the invention is administration of a compound of formula (I) or a pharmacologically acceptable salt thereof for the treatment of a disease of the peripheral and/or central nervous system related to inflammation. Included in this aspect of the invention is the treatment of cerebral vasculitis, multiple sclerosis, autoimmune ophthalmitis and polyneuropathia. Comprised by the invention is also the administration of a compound of the invention for the treatment of an inflammation of the central nervous system to prevent apoptotic cell death. Moreover, as some of the compounds of the invention show a distinct ability to induce nerve regeneration, positive treatment effects are often seen in central nervous system diseases involving damage of cells in this region. This aspect of the invention also includes treatment of traumatic injuries to the central nervous system, brain edema, multiple sclerosis, Alzheimer's disease, bacterial and viral infections in the central nervous system, stroke, and haemorrhagia in the central nervous system.

Comprised by the invention is also the administration of a compound of formula (I) or a pharmacologically acceptable salt thereof for the treatment of diseases of the eye and tear glands related to inflammation. Specific examples of such diseases comprise anterior and posterior uveitis, retinal vasculitis, optic neuritis, optic neuromyelitis, Wegener's granulomatosis, Sjögren's syndrome, episcleritis, scleritis, sarcoidosis affecting the eye and polychondritis affecting the eye.

Comprised by the invention is also the administration of a compound of formula (I) or a pharmacologically acceptable salt thereof for the treatment of diseases of the ear related to inflammation, specific examples of which include polychondritis affecting the ear and external otitis.

Comprised by the invention is also the administration of a compound of formula (I) or a pharmacologically acceptable salt thereof for the treatment of diseases of the nose related to inflammation, specific examples of which are sarcoidosis, polychondritis and mid-line granuloma of the nose.

Comprised by the invention is also the administration of a compound of formula (I) or a pharmacologically acceptable salt thereof for the treatment of diseases related to inflammation of the mouth, pharynx and salivary glands. Specific examples include Wegener's granulomatosis, midline granuloma, Sjögren's syndrome and polychondritis in these areas.

Included in the invention is also the administration of a compound of formula (I) or a pharmacologically acceptable salt thereof for the treatment of diseases related to inflammation in the lung. Specific examples include treatment of idiopathic alveolitis, primary pulmonary hypertension, bronchitis, chronic bronchitis, sarcoidosis, alveolitis in inflammatory systemic disease, pulmonary hypertension in inflammatory systemic disease, Wegener's granulomatosis and Good Pastures' syndrome.

Comprised by the invention is also the administration of a compound of formula (I) or a pharmacologically acceptable salt thereof for the treatment of diseases related to the inflammation of the heart. Specific examples include treatment of pericarditis, idiopathic pericarditis, myocarditis, Takayasus' arteritis, Kawasaki's disease, coronary artery vasculitis, pericarditis in inflammatory systemic disease, myocarditis in inflammatory systemic disease, endocarditis and endocarditis in inflammatory systemic disease.

Comprised by the invention is also the administration of a compound of formula (I) or a pharmacologically acceptable salt thereof for the treatment of diseases related to inflammation of the liver. Specific examples include treatment of hepatitis, chronic active hepatitis, biliary cirrhosis, hepatic damage by toxic agents, interferon induced hepatitis, hepatitis induced by viral infection, liver damage induced by anoxia and liver damage caused by mechanical trauma.

Comprised by the invention is also the administration of a compound of formula (I) or a pharmacologically acceptable salt thereof for the treatment of diseases related to inflammation of the pancreas. Specific examples include treatment (and prevention) of diabetes mellitus, acute pancreatitis and chronic pancreatitis.

Comprised by the invention is also the administration of a compound of formula (I) or a pharmacologically acceptable salt thereof for the treatment of diseases related to the inflammation of the thyroidea. Specific examples of these embodiments of the invention include treatment of thyreoiditis, autoimmune thyreoiditis and Hashimoto's thyreoiditis.

Comprised by the invention is also the administration of a compound of formula (I) or a pharmacologically acceptable salt thereof for the treatment of diseases related to inflammation of the kidney. Specific examples include treatment of glomerulonephritis, glomerulonephritis in systemic lupus erythematosus, periarteritis nodosa, Wegener's granulomatosis, Good-Pastures' syndrome, HLAb27 associated diseases, IgA nephritis (IgA=Immunoglobulin A), pyelonephritis, chronic pyelonephritis and interstitial nephritis.

Comprised by the invention is also the administration of a compound of formula (I) or a pharmacologically acceptable salt thereof for the treatment of diseases related to the inflammation of the joints. Specific examples include treatment of Bechterew's disease, psoriatic arthritis, rheumatoid arthritis, arthritis in colitis ulcerosa, arthritis in morbus Crohn, affection of joints in systemic lupus erythematosus, systemic sclerosis, mixed connective tissue disease, reactive arthritis, Reiter's syndrome. Moreover, included in this embodiment of the invention is treatment of arthrosis of any joint, in particular arthrosis of finger joints, the knee and the hip.

Comprised by the invention is also the administration of a compound of formula (I) or a pharmacologically acceptable salt thereof for the treatment of diseases related to the inflammation of blood vessels. Specific examples include treatment of arteritis temporalis, periarteritis nodosa, arteriosclerosis, Takayasus' arteritis and Kawasaki's disease. Particularly advantageous is the capacity of some compounds of the invention to afford protection against and prevention of arteriosclerosis. This is in part due to the capacity of some compounds of Formula (I) or the pharmacologically acceptable salts thereof to prevent the induction of inducible nitric oxide synthesis (iNOS) caused by the action of oxidized Low Density Lipoprotein on endothelial cells and blood vessel walls.

Comprised by the invention is also the administration of a compound of the invention for the treatment of drug-induced disorders of the blood and lymphoid system, including the treatment of drug-induced hypersensitivity (including drug hypersensitivity) affecting blood cells and blood cell forming organs (e.g. bone marrow and lymphoid tissue). Specific embodiments of this aspect of the invention include the treatment of anemia, granulocytopenia, thrombocytopenia, leukopenia, aplastic anemia, autoimmune hemolytic anemia, autoimmune thrombocytopenia and autoimmune granulocytopenia.

The compounds of the invention may also be administered for the treatment of fast allergic disorders (Type I allergy). Included in this embodiment of the invention is the treatment of anaphylactic reactions, anaphylactoid reactions, asthma, asthma of allergic type, asthma of unknown origin, rhinitis, hay fever and pollen allergy.

Comprised by the invention is also the administration of a compound of formula (I) or a pharmacologically acceptable salt thereof for the treatment of inflammation related to infections of any origin. Specific examples include treatment of inflammation secondary to infection caused by virus, bacteria, helminths and protozoae.

Comprised by the invention is also the administration of a compound of formula (I) or a pharmacologically acceptable salt thereof for the treatment of inflammations related to trauma and/or tissue injury of any origin.

Compounds of formula (I) or pharmaceutically acceptable salts thereof have valuable pharmacological properties, making them useful for the treatment of disorders of the cardiovascular system such as disorders related to blood pressure, heart rate, vascular tone, natriuresis, bleeding, shock, disorders related to ischemia, infarction, repercussion injuries, arrhythmias of the heart, in particular during ischemia, or for the treatment of arrhythmias associated with reoxygenation of a previously ischemic period of the heart.

Compounds of formula (I) or the pharmaceutically acceptable salts thereof have valuable pharmacological properties, making them useful for the treatment of pain such as pain of central origin, pain seen after damage to the CNS, stroke, infarction, pain of peripheral origin, chronic pain, neuropathies and disorders where a treatment effect is achieved by stimulation of receptors in the periaqueductal grey area.

Because of the capacity of compounds of the invention to stimulate pigment formation in epidermal cells, some of the compounds of the invention may be also useful for inducing skin tanning for cosmetic reasons, for treatment of vitiligo, or any other condition where darkening of skin color is desired. Moreover, because of the ability of some of the compounds of the invention to inhibit pigment formation in cells of the skin, they may also be useful for inducing lighter skin color for cosmetic reasons, or during any condition where a lighter color of skin is desired.

Compounds of formula (I) or the pharmaceutically acceptable salts thereof have valuable pharmacological properties, making them useful to cause skin tanning, darkening the colour of the skin, to induce melanin synthesis in the skin, to reduce skin tanning, lightening the colour of the skin, to reduce or block melanin synthesis in the skin, to cause anti-inflammatory actions in the skin, to modulate epidermal growth, to improve wound healing, to treat acne, seborrhoea, acne roseacea, conditions related to malfunctions of the glands of the skin, e.g. sebacous glands and over or underproduction of sebum.

Compounds of the invention are useful for inhibiting or stimulating the in vivo formation of second messenger elements such as cAMP. Such inhibition/stimulation may be used in cells or crushed cell systems in vitro, e.g. for analytical or diagnostic purposes.

For analytical and diagnostic purposes the compounds of the invention may be used in radioactive form where they comprise one or more radioactive labels or gamma or positron emitting isotopes, to be used in radioligand binding for the quantification as well as tissue localisation of MC-receptors, for analysis of dissociation/association constants, and for imaging of in vivo binding by the use of scintigraphy, positron emission tomography (PET) or single photon emission computed tomography (SPECT), or for the diagnosis of disease and treatment of any malignancy where the malignant cells contain MC receptors.

Alternatively the compounds of the invention can be labelled with any other type of label that allows detection of the respective compound, e.g. fluorescence, biotin, NMR, MRI, or labels activated by gamma-irradiation, light photons or biochemical processes, or by light or UV-light (the latter in order to obtain a compound useful for covalent labelling of MC receptors by a photoaffinity technique).

Compounds of formula (I) or the pharmacologically acceptable salts thereof may also be tagged with a toxic agent (i.e. doxorubicin, ricin, diphtheria toxin or other) and used for targeted delivery to malignant cells bearing MC receptors, or tagged with a compound capable of activating the endogenous immune system for triggering the immune system (for example a compound, monoclonal antibody or other, capable of binding to a T-cell antigen, e.g. CD3 or other) for treatment of malignancies and other MC receptor expressing diseases. The thus formed hybrid compound will direct cytotoxic cells to the malignant melanoma cells or the MC1-receptor bearing malignant cells and inhibit the tumor growth.

Compounds of formula (I) or a pharmacologically acceptable salt thereof may be attached to the antibody chemically by covalent or non-covalent bond(s).

Compounds of the invention may be used for the treatment and diagnosis of diseases, disorders and/or pathological conditions in an animal, in particular in man.

The present invention also relates to a pro-drug which, upon administration to an animal or a human, is converted to a compound of the invention. Pro-drugs of the compounds of Formula (I) and their pharmacologically acceptable salts may be used for the same purposes as described in this specification for the compounds of the invention, as well as is disclosed in the Examples given below.

The compounds of the present invention may be bound covalently or non-covalently to one or several of other molecule(s) of any desired structure(s); the thus formed modified compound or complex may be used for the same purposes as described in this specification for the compounds of the invention, as well as is disclosed in the Examples given below. In a particularly important embodiment of the invention, a radioactively-labelled molecule is covalently bound to a compound of Formula (I) or a pharmacologically acceptable salt thereof so as to make a compound of Formula (I) or a pharmacologically acceptable salt thereof radioactively labelled.

Some of the compounds of the invention have an effect on xanthine oxidase in mammals, including humans.

The invention also relates to processes for the manufacture of and pharmaceutical preparations comprising one or more of the compounds of the invention, as well as to their uses for various medical and veterinary practices related to melanocyte stimulating hormone receptors.

Compounds of the general formula II are either commercially available or can be synthesised by methods well known in the art, see for example "Advanced Organic Chemistry", by Jerry March or "Organic Synthesis" by Michael B. Smith.

METHODS OF PREPARATION

We further provide a process for the preparation of a compound of formula (I) as defined in above, in which a compound of formula (II) wherein X, $R_1$, $R_2$, $R_3$, $R_4$ and $R_5$ are as previously defined, is reacted with an aminoguanidine (III), or a salt or protected form thereof, using procedures known per se in the art, and, following deprotection if necessary or desired, a compound of formula (I) is obtained.

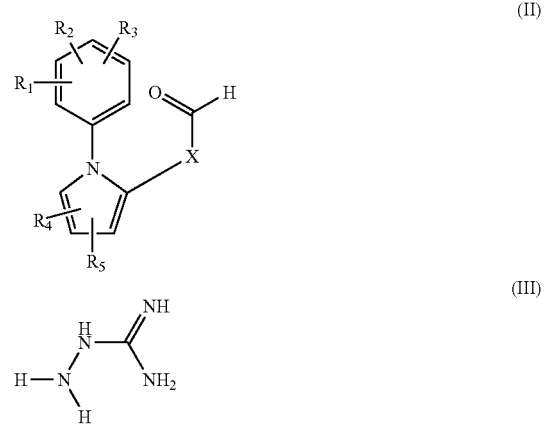

The following examples are intended to illustrate but not to limit the scope of the invention, although the compounds named are of particular interest for the intended purposes. The preparation of the compounds of general formula (I) is presented schematically in Example 1 below. Specific synthetic procedures are given in methods 1–3. The compounds are numbered and listed with their complete name below.

EXAMPLES

Example 1

The compounds of the invention may be prepared by the following general method. IR, NMR, MS and elementary analysis have confirmed the structures of the compounds. When melting points (m.p.) are given, these are uncorrected.

Example 1

N-[1-((4-Chlorophenyl)-1H-Pyrrol-2-yl)methylene-amino]guanidine 5 g (24.3 mmol) 1-(4-chlorophenyl)-pyrrol-2-carboxaldehyde and 4.96 g (36.5 mmol) aminoguanidine bicarbonate was suspended in 500 ml acetonitrile. 120 ml acetic acid was added and the reaction mixture was refluxed for 2 h. The solution was cooled and the solvent was evaporated. The resulting crude product was dissolved in ether and crystallised after four hours in the freezer. The slightly yellow solid was recrystallised from acetonitrile/ethanol (5:1) to give the pure product (1) as white crystals. Yield 3 g (45%).

The novel compounds 2–50 were prepared in an analogous manner:

Compounds 1–50

| No. | Name |
|---|---|
| 1 | N-{1-[(4-Chlorophenyl)-1H-Pyrrol-2-yl]methyleneamino}guanidine |
| 2 | N-[1-(5-propylamino-1-(2-butoxy-phenyl)-1H-pyrrol-2-yl)-methyleneamino]-guanidine |
| 3 | N-{3-[1-(2-Isobutyryl-phenyl)-5-nitro-1H-pyrrol-2-yl]-propylideneamino}-guanidine |
| 4 | N-{1-[1-(3-Cyanophenyl)-5-trifluoromethyl-1H-pyrrol-2-yl]-methyleneamino}-guanidine |
| 5 | N-{3-[1-(3-Fluorophenyl)-5-methyl-1H-pyrrol-3-yl]- |

-continued

| No. | Name |
|---|---|
|  | propylideneamino}-guanidine |
| 6 | N-[1-(4-Aminophenyl)-5-hydroxy-1H-pyrrol-2-ylmethylideneamino]-guanidine |
| 7 | N-{3-[1-(4-Chlorophenyl)-5-phenethyl-1H-pyrrol-3-yl]-propylideneamino}-guanidine |
| 8 | N-{3-[1-(4-Propylaminophenyl)-5-trichloromethyl-1H-pyrrol-3-yl]-propylideneamino}-guanidine |
| 9 | N-(5-tert-Butyl-1-phenyl-1H-pyrrol-2-ylmethylideneamino)-guanidine |
| 10 | N-[3-(5-Methoxy-1-phenyl-1H-pyrrol-3-yl)-propylideneamino]-guanidine |
| 11 | N-[4-Pentyl-1-(2-trichloromethylphenyl)-1H-pyrrol-3-ylmethylideneamino]-guanidine |
| 12 | N-(4-Cyano-1-o-tolyl-1H-pyrrol-3-ylmethylideneamino)-guanidine |
| 13 | N-{3-[4-Hydroxy-1-(3-trichloromethylphenyl)-1H-pyrrol-2-yl]-propylideneamino}-guanidine |
| 14 | N-{3-[1-(3-tert-Butylphenyl)-5-isobutyryl-1H-pyrrol-2-yl]-propylideneamino}-guanidine |
| 15 | N-(1-Biphenyl-4-yl-4-chloro-1H-pyrrol-2-ylmethylideneamino)-guanidine |
| 16 | N-{3-[1-(4-Bromophenyl)-4-tert-butyl-1H-pyrrol-3-yl]-propylideneamino}-guanidine |
| 17 | N-(4-Butoxy-1-phenyl-1H-pyrrol-3-ylmethylideneamino)-guanidine |
| 18 | N-[3-(4-Methoxy-1-phenyl-1H-pyrrol-2-yl)-propylideneamino]-guanidine |
| 19 | N-{3-[1-(2-Nitrophenyl)-1H-pyrrol-2-yl]-propylideneamino}-guanidine |
| 20 | N-{3-[1-(2-Hydroxyphenyl)-1H-pyrrol-2-yl]-propylideneamino}-guanidine |
| 21 | N-[1-(3-Methoxyphenyl)-1H-pyrrol-2-ylmethylideneamino]-guanidine |
| 22 | N-[1-(3-Butylaminophenyl)-1H-pyrrol-3-ylmethylideneamino]-guanidine |
| 23 | N-[1-(4-tert-Butylphenyl)-1H-pyrrol-3-ylmethylideneamino]-guanidine |
| 24 | N-{3-[1-(4-Trifluoromethylphenyl)-1H-pyrrol-2-yl]-propylideneamino}-guanidine |
| 25 | N-(1-Phenyl-1H-pyrrol-3-ylmethylideneamino)-guanidine |
| 26 | N-[3-(1-Phenyl-1H-pyrrol-2-yl)-propylideneamino]-guanidine |
| 29 | N-[3-(4-Methyl-1-phenyl-1H-pyrrol-3-yl)-propylideneamino]-guanidine |
| 30 | N-[1-(3-Nitro-4-propylaminophenyl)-1H-pyrrol-3-ylmethylideneamino]-guanidine |
| 31 | N-{3-[1-(3-Butylamino-4-methylphenyl)-4-methyl-1H-pyrrol-2-yl]-propylidene}-guanidine |
| 32 | N-{3-[5-Bromo-1-(4-bromophenyl)-1H-pyrrol-3-yl]-propylideneamino}-guanidine |
| 33 | N-[(5-Chloro-1-(4-isobutyrylphenyl)-4-pentyl-1H-pyrrol-2-yl)methyleneamino]-guanidine |
| 34 | N-[3-(5-Propoxy-1-m-tolyl-1H-pyrrol-2-yl)-propylideneamino]-guanidine |
| 35 | N-[4-Methyl-5-propylamino-1-(3-trichloromethylphenyl)-1H-pyrrol-3-ylmethylideneamino]-guanidine |
| 36 | N-{3-[1-(3-Nitrobiphenyl-4-yl)-1H-pyrrol-2-yl]-propylideneamino}-guanidine |
| 37 | N-{2-[4-tert-Butyl-1-(4-methoxy-2-propylaminophenyl)-1H-pyrrol-3-yl]-ethylideneamino}-guanidine |
| 38 | N-{3-[1-(2-Bromo-3-chlorophenyl)-1H-pyrrol-3-yl]-propylideneamino}-guanidine |
| 39 | N-[4-Bromo-1-(2-butoxy-3-propoxyphenyl)-1H-pyrrol-2-ylmethylideneamino]-guanidine |
| 40 | N-[5-Hydroxy-1-(2-hydroxyphenyl)-1H-pyrrol-3-ylmethylideneamino]-guanidine |
| 41 | N-{3-[1-(2-tert-Butylphenyl)-4-chloro-5-methyl-1H-pyrrol-2-yl]-propylideneamino}-guanidine |
| 42 | N-[5-Isobutyryl-1-(2,3,4-trimethoxyphenyl)-1H-pyrrol-2-ylmethylideneamino]-guanidine |
| 43 | N-{3-[5-tert-Butyl-1-(2-tert-butyl-3,4-bis-trichloromethylphenyl)-4-trichloromethyl-1H-pyrrol-2-yl]-propylideneamino}-guanidine |
| 44 | N-{2-[1-(4-Pyrrol-1-ylphenyl)-1H-pyrrol-2-yl]-ethylideneamino}-guanidine |
| 45 | N-[1-(4-Morpholin-4-yl-phenyl)-1H-pyrrol-2-ylmethylideneamino]-guanidine |
| 46 | N-[1-(4-Pyrrolidin-1-yl-phenyl)-1H-pyrrol-3-ylmethylideneamino]-guanidine |
| 47 | N-((1-Phenyl-1H-pyrrol-2-yl)methyleneamino)guanidine |
| 48 | N-[(1-(4-Trifluoromethylphenyl)-1H-pyrrol-2-yl)methyleneamino]guanidine |
| 49 | N-[(1-(3-cyanophenyl)-1H-pyrrol-2-yl)methyleneamino]guanidine |
| 50 | N-[(1-(3,5-dichlorophenyl)-1H-pyrrol-2-yl)methyleneamino]guanidine |

Test 1. Affinity for the MC1-receptor

The binding assay was carried out essentially as described by Lunec et al, Melanoma Res 1992; 2; 5–12 using $I^{125}$-NDP-αMSH as ligand.

Test 2. Affinity for the MC3-receptors, the MC4-receptors and the MC5-receptors

The binding assays were carried out essentially as described by Szardenings et al, J Biol Chem 1997; 272; 27943–27948 and Schiöth et al, FEBS Lett 1997; 410; 223–228 using I125-NDP-αMSH as ligand.

Test 3. cAMP

The stimulation of cAMP was carried out essentially as described by Schiöth et al, Br J Pharmacol 1998; 124; 75–82, however, the response is given relative to α-MSH.

TABLE 1a

Affinity for MC-receptors

| Compound | Ki (μM) | | | |
|---|---|---|---|---|
|  | MC1 | MC3 | MC4 | MC5 |
| 1 | 0.42 | 15.6 | 5.1 | 17.5 |
| 48 | 1.20 |  | 0.07 | 7.8 |
| 50 | 0.70 | 12.84 | 3.60 | 7.52 |

TABLE 1b

Influence on cAMP

| Compound | cAMP agonist/plateau stim. α-MSH (%) | | | |
|---|---|---|---|---|
|  | MC1 | MC3 | MC4 | MC5 |
| 1 | 30 | 35 | 118 | 6 |
| 50 |  |  | 36 |  |

Example 2

In Vivo Effects on Food Intake

Compounds have been tested for their effects on food intake and body weight in rats. In order to investigate the agonistic effect, ie decrease in food intake, of compounds, the nocturnal protocol was used.

Sprague-Dawley, male rats were used, which were cannulated intracerebroventricularly. Stainless steel guide cannulae were placed in the lateral ventricle and fixed in the skull. Animals were acclimatized for a week before the experiments took place. After the experiments were done, the rats were killed and placement of the cannulae were checked.

Nocturnal Protocol:

Rats were cannulated as described above. They were used without prior starvation, and compounds were administered at 5 pm in a total volume of 5 ml. Doses of compound 2:4 used were 1, 4 and 10 nmoles. Food intake was measured at 3, 15 and 24 hours after dosing, and body weight was recorded at 24 hours. For comparison, the well known MC4 receptor agonist, Melanotan II (MTII) was used, at a dose of 1 nmole.

Example 3

Anti Inflammatory Effects

Control

Female BALB/c mice (weight 20–22 g) were sensitized by treatment of the shaved abdomen with 30 μl of 0.5% 2,4-dinitrofluorobenzene (DNFB). After 4 days they were challenged with 10 μl of 0.3% DNFB to the paw. The unchallenged mice paws served as a control. Twenty-four hours after the last challenge, the difference in paws weight were determined as an indicator of the inflammation (paw edema).

Alpha-MSH and Prednisolone Controls

Mice were treated as the control but were additionally injected i.p. with α-MSH (0.5 mg/kg) or prednisolone (20 mg/kg) two hours before sensitization (day 0) and the same dose was administered repeatedly after sensitization during four consecutive days. The paw edema inhibition was measured as described above.

Study of New Compounds

Mice were treated as the control but were additionally injected i.p. with various doses (0.05, 0.15 or 0.25, 0.375, 0.5 and 0.75 mg/kg) of each compounds two hours before sensitization (day 0) and the same dose was administered repeatedly after sensitization during four consecutive days. The paw edema inhibition as described above. Groups containing at least 10 mice each were used for all experiments.

Example 4

The following formulations are representative for all of the pharmacologically active compounds of the invention Example of a Preparation Comprising a Capsule

| | Per capsule |
|---|---|
| Active ingredient, as salt | 5 mg |
| Lactose | 250 mg |
| Starch | 120 mg |
| Magnesium stearate | 5 mg |
| Total | 380 mg |

In case of higher amounts of active ingredient, the amount of lactose used may be reduced.

Example of a Suitable Tablet Formulation

| | Per tablet |
|---|---|
| Active ingredient, as salt | 5 mg |
| Potato starch | 90 mg |
| Colloidal Silica | 10 mg |
| Talc | 20 mg |
| Magnesium stearate | 2 mg |
| 5% aqueous solution of gelatine | 25 mg |

| | Per tablet |
|---|---|
| Total | 152 mg |

The invention claimed is:

1. A compound of the formula (I) and tautomeric forms thereof:

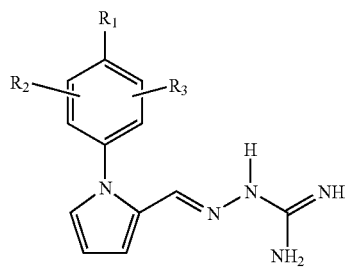

(I)

wherein $R_1$ is selected from the group consisting of halogen, alkyl having 1 to 5 carbon atoms, alkoxy having 1 to 5 carbon atoms, hydroxy, alkylsulphonyloxy, cyano, nitro, trihaloalkyl, sulpho, and any of the following structures:

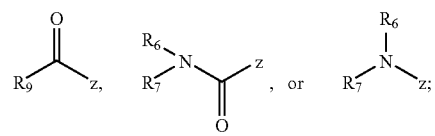

wherein $R_9$ is selected from the group consisting of alkyl having 1 to 5 carbon atoms alkoxy having 1 to 5 carbon atoms, hydroxy and primary amine, and wherein $R_6$ and $R_7$ are the same or different and are selected from the group consisting of hydrogen and alkyl having 1 to 5 carbon atoms, and wherein $R_2$ and $R_3$ are the same or different and are selected from the group consisting of hydrogen, halogen, alkyl having 1 to 5 carbon atoms, alkoxy having 1 to 5 carbon atoms, hydroxy, alkylsulphonyloxy, cyano, nitro, trihaloalkyl, sulpho, and any of the following structures:

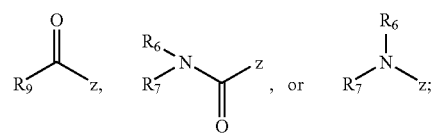

wherein $R_9$ is selected from the group consisting of alkyl having 1 to 5 carbon atoms, alkoxy having 1 to 5 carbon atoms, hydroxy and primary amine, and wherein $R_6$ and $R_7$ are the same or different and are selected from the group consisting of hydrogen and alkyl having 1 to 5 carbon atoms;

or a pharmaceutically acceptable salt thereof.

2. A compound as claimed in claim 1 wherein $R_1$ is alkyl having 1 to 5 carbon atoms, alkoxy having 1 to 5 carbon atoms, halogen or trihaloalkyl.

3. A compound as claimed in claim 2 wherein $R_1$ is halogen or trihaloalkyl.

4. A compound as claimed in claim 3 wherein halogen is chloro.

5. A compound as claimed in claim 3 wherein halogen is bromo.

6. A compound as claimed in claim 3 wherein trihaloalkyl is trifluoromethyl or trichloromethyl.

7. A compound as claimed in claim 6 wherein trihaloalkyl is trifluoromethyl.

8. A compound as claimed in claim 1 wherein alkyl is methyl, ethyl, n-butyl, n-pentyl or tert-butyl.

9. A compound as claimed in claim 1 wherein alkoxy is methoxy, ethoxy, propyloxy, butoxy or tert-butoxy.

10. A compound as claimed in claim 1 wherein $R_3$ is hydrogen.

11. A compound as claimed in claim 1, wherein $R_2$ and $R_3$ are hydrogen.

12. A compound as claimed in claim 11 wherein $R_1$ is alkyl having 1 to 5 carbon atoms, alkoxy having 1 to 5 carbon atoms, halogen or trihaloalkyl.

13. A compound as claimed in claim 11 wherein $R_1$ is halogen or trihaloalkyl.

14. A compound as claimed in claim 11 wherein halogen is chloro.

15. A compound as claimed in claim 11 wherein halogen is bromo.

16. A compound as claimed in claim 11 wherein trihaloalkyl is trifluoromethyl or trichloromethyl.

17. A compound as claimed in claim 16 wherein trihaloalkyl is trifluoromethyl.

18. A compound as claimed in claim 1 which is N-{1-[(4-Chlorophenyl)-1H-Pyrrol-2-yl]methyleneamino}guanidine; N-[1-(4-Aminophenyl)-5-hydroxy-1H-pyrrol-2-ylmethylideneamino]-guanidine; N-[4-Bromo-1-(2-butoxy-3-propoxyphenyl)-1H-pyrrol-2-ylmethylideneamino]-guanidine; N-[(1-(4-Trifluoromethylphenyl)-1H-pyrrol-2-yl)-methyleneamino]guanidine; or a pharmaceutically acceptable salt thereof.

19. A pharmaceutical composition comprising a compound as claimed in claim 1 together with one or more adjuvants, carriers or excipients.

* * * * *